(12) United States Patent
Cahan et al.

(10) Patent No.: US 10,593,231 B2
(45) Date of Patent: Mar. 17, 2020

(54) SYSTEM AND METHOD FOR MONITORING GASTRIC FULLNESS

(71) Applicant: INTERNATIONAL BUSINESS MACHINES CORPORATION, Armonk, NY (US)

(72) Inventors: Amos Cahan, Yorktown Heights, NY (US); Theodore Gerard Van Kessel, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1127 days.

(21) Appl. No.: 14/969,181

(22) Filed: Dec. 15, 2015

(65) Prior Publication Data

US 2017/0169725 A1    Jun. 15, 2017

(51) Int. Cl.
| | | |
|---|---|---|
| G09B 19/00 | (2006.01) | |
| A61B 8/08 | (2006.01) | |
| A61B 8/00 | (2006.01) | |
| A61B 5/145 | (2006.01) | |

(52) U.S. Cl.
CPC ...... *G09B 19/0092* (2013.01); *A61B 5/14532* (2013.01); *A61B 8/08* (2013.01); *A61B 8/4427* (2013.01); *A61B 8/5207* (2013.01); *A61B 8/56* (2013.01); *A61B 8/58* (2013.01); *A61B 8/4227* (2013.01)

(58) Field of Classification Search
CPC ......... G09B 19/0092; A61B 8/08; A61B 8/58; A61B 8/56; A61B 5/14532; A61B 8/4427; A61B 8/5207; A61B 8/4227

USPC .................................................. 600/437, 438
See application file for complete search history.

(56) References Cited

U.S. PATENT DOCUMENTS

| | | | | |
|---|---|---|---|---|
| 5,919,216 | A * | 7/1999 | Houben | A61B 5/14532 607/72 |
| 6,238,341 | B1 * | 5/2001 | Mullen | A61B 8/00 600/437 |
| 7,338,444 | B2 * | 3/2008 | Ben-Oren | A61B 5/083 600/300 |
| 7,946,976 | B2 | 5/2011 | Gertner | |

(Continued)

OTHER PUBLICATIONS

Perlas ["Validation of a Mathematical Model for Ultrasound Assessment of Gastric Volume by Gastroscopic Examination", www.anesthesia-analgesia.org, Feb. 2013, vol. 116, No. 2] (Year: 2013).*

(Continued)

*Primary Examiner* — Oommen Jacob
(74) *Attorney, Agent, or Firm* — F. Chau & Associates, LLC

(57) ABSTRACT

A system for monitoring stomach fullness includes an ultrasound transponder configured to transmit ultrasound signals and receive reflected ultrasound signals. A processor is configured to process the received reflected ultrasound signals to determine level of stomach fullness and output fullness data indicative of the determined level of stomach fullness. A memory stores calibration data representative of calibrated levels of stomach fullness including empty and full. A stored program has executable codes to, upon execution, control the ultrasound transponder, compare the fullness data against the calibration data, and output alert data upon a match of a preset fullness level.

20 Claims, 7 Drawing Sheets

(56) References Cited

U.S. PATENT DOCUMENTS

| | | | |
|---|---|---|---|
| 8,114,030 B2 | 2/2012 | Ales et al. | |
| 8,135,470 B2* | 3/2012 | Keinnel | A61N 1/36007 607/40 |
| 8,308,644 B2 | 11/2012 | McMorrow et al. | |
| 8,612,016 B2 | 12/2013 | Kliger et al. | |
| 9,743,880 B1* | 8/2017 | Euliano | G08B 23/00 |
| 10,118,035 B2* | 11/2018 | Perez | A61N 1/0492 |
| 2003/0208113 A1* | 11/2003 | Mault | A61B 5/14532 600/316 |
| 2004/0167416 A1* | 8/2004 | Lee | A61B 5/0031 600/513 |
| 2005/0096713 A1* | 5/2005 | Starkebaum | A61B 18/1492 607/100 |
| 2007/0179556 A1* | 8/2007 | Ben Haim | A61B 5/053 607/40 |
| 2008/0009913 A1* | 1/2008 | Errico | A61N 1/36007 607/40 |
| 2008/0077040 A1* | 3/2008 | Ales | A61B 5/103 600/546 |
| 2008/0077042 A1* | 3/2008 | Feldkamp | A61B 5/103 600/547 |
| 2008/0086076 A1* | 4/2008 | Gerber | A61J 15/0003 604/43 |
| 2008/0097188 A1* | 4/2008 | Pool | A61B 5/05 600/409 |
| 2008/0097249 A1* | 4/2008 | Pool | A61B 5/05 600/586 |
| 2008/0264180 A1* | 10/2008 | Gakhar | A61B 5/4205 73/861.18 |
| 2010/0063842 A1* | 3/2010 | Carroll | A61B 5/7435 705/3 |
| 2011/0034760 A1 | 2/2011 | Brynelsen et al. | |
| 2011/0125063 A1 | 5/2011 | Shalon et al. | |
| 2012/0065479 A1 | 3/2012 | Lahiji et al. | |
| 2012/0143021 A1* | 6/2012 | Nagar | A61B 5/14532 600/301 |
| 2012/0157843 A1* | 6/2012 | Lavin | A61B 8/465 600/443 |
| 2012/0191038 A1* | 7/2012 | Gerber | A61B 5/1071 604/67 |
| 2012/0259389 A1* | 10/2012 | Starkebaum | A61B 5/0006 607/62 |
| 2012/0296210 A1* | 11/2012 | Pelissier | A61B 8/00 600/438 |
| 2013/0102930 A1* | 4/2013 | Connor | A61B 1/267 600/590 |
| 2013/0184587 A1* | 7/2013 | Eom | A61B 8/4411 600/443 |
| 2013/0310706 A1* | 11/2013 | Stone | A61B 8/56 600/561 |
| 2014/0303460 A1* | 10/2014 | Corley | A61B 5/6828 600/301 |
| 2015/0073285 A1* | 3/2015 | Albert | A61B 5/0408 600/509 |
| 2016/0012749 A1* | 1/2016 | Connor | G09B 5/00 600/13 |
| 2016/0143817 A1* | 5/2016 | Elia | A61J 15/0084 604/503 |
| 2016/0174866 A1* | 6/2016 | Chan | A61B 5/1077 600/301 |
| 2016/0213302 A1* | 7/2016 | Frushour | A61B 5/4238 |
| 2017/0169725 A1* | 6/2017 | Cahan | G09B 19/0092 |
| 2017/0215842 A1* | 8/2017 | Ryu | A61B 8/06 |
| 2018/0078195 A1* | 3/2018 | Sutaria | A61B 5/0402 |

OTHER PUBLICATIONS

Van De Puttte ["Ultrasound assessment of gastric content and volume", British Journal of Anaesthesia 113 (1): 12-22 (2014)] (Year: 2014).*

Tefera ["Gastric Accommodation Studied by Ultrasonography in Patients with Reflux Esophagitis " Digestive Diseases and Sciences , vol. 46, No. 3 (Mar. 2001), pp. 618-625] (Year: 2001).*

Perella ["Repeatability of Gastric Volume Measurements and Intragastric Content Using Ultrasound in Preterm Infants"] JPGN vol. 59, No. 2, Aug. 2014 (Year: 2014).*

Robert ["Simultaneous Assessment of Liquid Emptying and Proximal Gastric Tone in Humans" Gastroenterology 1993;105: 667-674] (Year: 1993).*

Mell, Peter, and Grance, Timothy. "The NIST definition of cloud computing." (2011).

* cited by examiner

SYSTEM AND METHOD FOR MONITORING GASTRIC FULLNESS

BACKGROUND

Exemplary embodiments of the present invention relate to a system and method for monitoring gastric fullness. More particularly, exemplary embodiments of the present invention relate to a system and method for monitoring gastric fullness using ultrasound scanning of an individuals' stomach.

Overeating may lead to an uncomfortable feeling of heaviness, nausea, vomiting and obesity. Generally, a feeling of fullness may be delayed, and so an individual may feel full only after they have overeaten. Thus, an individual may unintentionally consume a greater volume of food than the volume of the user's stomach. Various stimuli such as smell, sight and taste of food, as well as psychological drivers may also lead to an individual suppressing, ignoring or overriding a feeling of fullness, leading to overfilling of the stomach.

Overeating may be closely related to intake of an excessive volume of food with relation to stomach volume. The degree of stomach filling or fullness may be subjectively determined by individuals while they are consuming food, and such a subjective determination may include a time delay in which fullness is not subjectively experienced by the individual until after an excessive volume of food has already been consumed. The steep rise in obesity prevalence suggests that subjective determination of fullness may be insufficient to control overeating.

It may be desirable for individuals to objectively measure the degree of stomach filling in real time.

SUMMARY

Exemplary embodiments of the present invention provide a system for monitoring stomach fullness including an ultrasound transponder configured to transmit ultrasound signals and receive reflected ultrasound signals. A processor is configured to process the received reflected ultrasound signals to determine level of stomach fullness and output fullness data indicative of the determined level of stomach fullness. A memory stores calibration data representative of calibrated levels of stomach fullness including empty and full. A stored program has executable codes to, upon execution, control the ultrasound transponder, compare the fullness data against the calibration data, and output alert data upon a match of a preset fullness level.

According to an exemplary embodiment of the present invention the stored program or the ultrasound transponder may be embedded in a smartphone.

According to an exemplary embodiment of the present invention the smartphone may execute the stored program to output the alert data audibly or visually.

According to an exemplary embodiment of the present invention the smartphone may execute the stored program to activate the ultrasound transponder at a preset interval including continuously or upon user activation.

According to an exemplary embodiment of the present invention at least one of the memory or the stored program may be cloud-based and may be accessible via wireless communication.

According to an exemplary embodiment of the present invention a wifi signal may be configured to establish communication with a portable processing device.

According to an exemplary embodiment of the present invention the portable processing device may be at least one of a smartphone, a smart wearable device, a smart tablet, or a laptop computer.

According to an exemplary embodiment of the present invention the portable processing device may execute the stored program to output the alert data audibly or visually.

According to an exemplary embodiment of the present invention the portable processing device may execute the stored program to activate the ultrasound transponder at a preset interval including continuously or upon user activation.

According to an exemplary embodiment of the present invention the processor may execute the stored program to perform analysis of the fullness data in connection with glucose data received from an external device.

According to an exemplary embodiment of the present invention the ultrasound transponder may be adhered or strapped to a portion of a user's skin proximal to the user's stomach.

According to an exemplary embodiment of the present invention an accelerometer may determine the position of the user.

Exemplary embodiments of the present invention provide a method of monitoring stomach fullness including transmitting ultrasound signals to a stomach. Reflected ultrasound signals may be received. The received reflected ultrasound signals may be processed to determine a level of stomach fullness. Fullness data indicative of the determined level of stomach fullness may be output. Calibration data representative of calibrated levels of stomach fullness including empty and full may be stored. The fullness data may be compared against the calibration data. Alert data may be output upon a match of a preset fullness level.

According to an exemplary embodiment of the present invention a method of monitoring stomach fullness may include wirelessly transmitting the fullness data to a processing device.

According to an exemplary embodiment of the present invention a method of monitoring stomach fullness may include wirelessly communicating from the processing device a control signal to control transmitting ultrasound signals at a preset interval including continuously or upon user activation.

According to an exemplary embodiment of the present invention alert data may be audibly or visibly presented at the processing device.

According to an exemplary embodiment of the present invention calibration data may be stored at a remote cloud-based storage device.

According to an exemplary embodiment of the present invention a method of monitoring stomach fullness may include comparing the fullness data against the calibration data at a remote cloud-based processing device.

According to an exemplary embodiment of the present invention fullness data may be analyzed in connection with glucose data received from an external device.

According to an exemplary embodiment of the present invention a method of monitoring stomach fullness may include determining a position of user by an accelerometer in connection with calibrating levels of stomach fullness.

BRIEF DESCRIPTION OF THE DRAWINGS

The above and other features of the present invention will become more apparent by describing in detail exemplary embodiments thereof, with reference to the accompanying drawings, in which.

DETAILED DESCRIPTION

Figure 1:
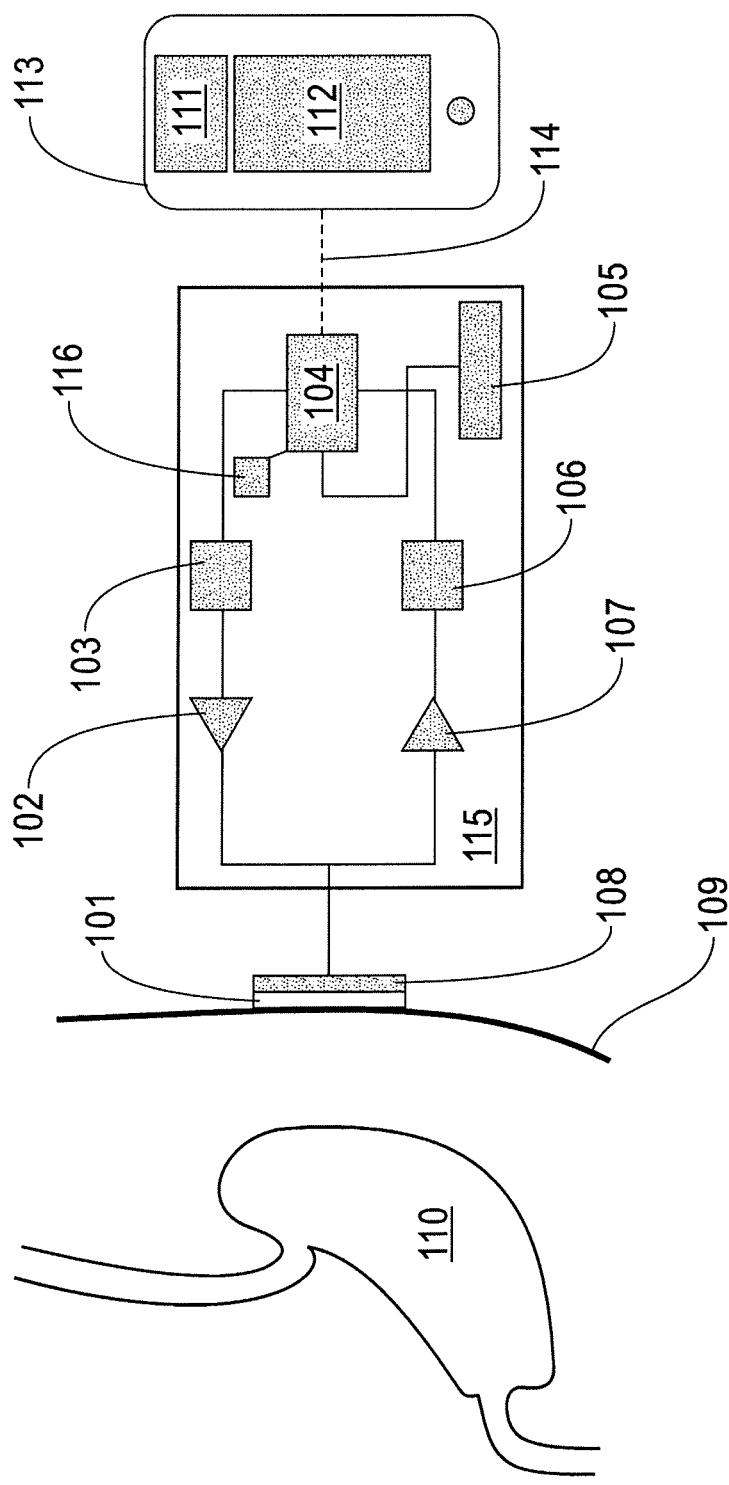
FIG. 1 illustrates a system for monitoring stomach fullness according to an exemplary embodiment of the present invention.

Exemplary embodiments of the present invention relate to a system and method for monitoring the volume of stomach content using ultrasound technology and for providing feedback to a user on the degree to which the stomach is full as well as advice when to refrain from additional intake. Thus, overeating may be reduced or prevented.

According to an exemplary embodiment of the present invention, it may be determined whether the stomach is empty prior to medical procedures that require an empty stomach such as sedation, anesthesia and use of substances such as contrast material.

According to an exemplary embodiment of the present invention, it may be determined if there is acute increase in the stomach volume, a condition termed "acute gastric dilatation," which may accompany several serious clinical conditions and may result in respiratory compromise, gastric ischemia, gastric perforation and death. Prompt recognition of acute gastric dilatation allows for decompression and prevention of complications (e.g., by insertion of a nasogastric tube).

In medical practice, it may be desirable to determine whether there is content in the stomach of an individual. For example, when there is risk for aspiration of stomach content into the lungs, such as in medical interventions associated with nausea or with compromising of reflexes that prevent aspiration. For example, intubation of the trachea when there is content in the stomach is associated with a risk for aspiration. Procedures associated with a risk for aspiration may be deferred, if possible, until the stomach is empty. If the procedure cannot be delayed, then protective measures may be taken. For example, intubation when stomach is full may include external compression of the trachea against the esophagus to prevent food from regurgitating. It may be desirable to have a simple, quick and reliable way for caregivers with little or no expertise in operating ultrasound devices to assure that the stomach of an individual is empty before performing certain medical interventions. Similarly, it may be desirable to have a simple, quick and reliable way for caregivers with little or no expertise in operating ultrasound devices to determine whether there is acute gastric dilatation.

Exemplary embodiments of the present invention will be described in more detail below with reference to the accompanying drawings. Like reference numerals may refer to like elements throughout the specification and drawings.

FIG. 1 illustrates a system for monitoring stomach fullness according to an exemplary embodiment of the present invention.

Referring to FIG. 1, a system for monitoring stomach fullness may include an ultrasound transponder 108 (e.g., a piezo ultrasonic transducer) coupled to the skin 109 of an individual by a securing part 101 to measure the content of the individual's stomach 110. The ultrasound transponder 108 may include a piezo ultrasonic transducer system 115. The piezo ultrasonic transducer system 115 may include a frequency generator 103, a first amplifier 102, a second amplifier 107, an analog to digital converter 106, a power source 105, a memory 116 and a microprocessor 104.

The system for monitoring stomach fullness may be a standalone device or may be embedded in a remote device 113 (e.g., a smartphone or smart watch) to receive operating instructions. The remote device 113 may include a display 112 and a remote device microprocessor 111. The piezo ultrasonic transducer system 115 may include a communication part 114 for communicating with the remote device 113. The communication part 114 may be configured to communicate with the remote device 113 through a wired connection (e.g., a USB connection) or a wireless connection (e.g., wifi or Bluetooth). The piezo ultrasonic transducer system 115 may provide a signal to the ultrasound transponder 108 and may receive a signal from the ultrasound transponder 108.

According to an exemplary embodiment of the present invention the stored program and/or the ultrasound transponder 108 may be embedded in the remote device 113 (e.g., the smartphone). The remote device 113 including the stored program and the ultrasound transponder 108 may operate as the standalone device, and thus the remote device 113 may monitor stomach fullness.

Exemplary embodiments of the present invention provide a system for monitoring stomach fullness. The system may include the ultrasound transponder 108 configured to transmit ultrasound signals and receive reflected ultrasound signals. A processor (e.g., the microprocessor 104 or the remote device microprocessor 111) may be configured to process the received reflected ultrasound signals to determine level of stomach fullness and output fullness data indicative of the determined level of stomach fullness. The memory 116 may store calibration data representative of calibrated levels of stomach fullness including empty and full. A stored program may have executable codes to, upon execution, control the ultrasound transponder 108, compare the fullness data against the calibration data, and output alert data upon a match of a preset fullness level. The stored program may be stored in a memory in the piezo ultrasonic transducer system 115 (e.g., when the ultrasound transponder 108 is a standalone device) or may be stored in the remote device 113. The stored program may be stored in the cloud and may be accessed by the ultrasound transponder 108 or by the remote device 113. Cloud storage is discussed below in more detail.

According to an exemplary embodiment of the present invention an input frequency may be applied to the first amplifier 102 that applies an impedance matched input signal to the ultrasound transponder 108. The ultrasound transponder 108 may vibrate in response to the voltage input from the first amplifier 102, thus producing an ultrasonic acoustic signal. By varying the input frequency, it is possible to examine the acoustic transmission spectrum of the stomach compartment. This may be performed over a range of frequencies, for example, from 25 kHz to 1.5 MHz. The reflected acoustic signal may be captured by the ultrasound transponder 108 and may cause a voltage to be produced in the ultrasound transponder 108 that is compared to the voltage input. The reflected acoustic signal may be analyzed by a digital computer (e.g., the microprocessor 104) and an analysis may be output (e.g., wirelessly transmitted) to the external device 113 (e.g., a smartphone, a laptop or a cloud service) using ultrasound waves, IR, Bluetooth, or RFID.

According to an exemplary embodiment of the present invention, the power source 105 may include at least one of a utility outlet, a battery, a solar panel, an ultra capacitor and a generator.

According to an exemplary embodiment of the present invention a plurality of ultrasonic emitter/receiver elements may be used to detect stomach fullness, which may increase spatial resolution and dimensionality. A system according to an exemplary embodiment of the present invention may act as a simple audio (~15 Hz to 50 kHz) detector to listen to stomach sounds directly. The system according to an exemplary embodiment of the present invention may include a miniature ultrasound transponder placed on the skin of an individual in proximity to the individual's stomach (e.g., on the individuals abdomen).

According to an exemplary embodiment of the present invention the system may operate in an M-mode to determine the distance between the walls of the stomach, or may employ 1D, 2D or 3D ultrasound technology to estimate the volume of the stomach. The input signal may be applied continuously or intermittently. The ultrasound transponder 108 may be glued to the abdominal wall (e.g. using adhesive tape), secured to the user's skin 109 (e.g., the user's abdominal wall) with a strap or belt, or be held in place when desired by a user. The system according to an exemplary embodiment of the present invention may alert the user by vibration or sound when the stomach fullness reaches a predetermined threshold. The system may capture, record and transmit this information to another device with storage, analysis and display part (e.g. a smartphone) to provide the user with feedback on the degree of filling of the stomach.

A system according to an exemplary embodiment of the present invention may include a vibrating device or part for producing a sound alert to alert the user to stomach fullness or when the system detects that a predetermined fullness threshold is reached. The predetermined fullness threshold may be set according to user preferences and may be any desired fullness threshold. For example, the user may set the system to provide both a sound and a vibration alert when the piezo ultrasonic transducer system 115 detects that the user's stomach is 90% full.

The communication part 114 according to an exemplary embodiment of the present invention may be a part for wireless communication (including ultrasound, WiFi, Bluetooth) with another device such as a smartphone, smart watch, computer or cloud server.

The piezo ultrasonic transducer system 115 according to an exemplary embodiment of the present invention may include an accelerometer to determine a position of the user or a position of the ultrasound transponder 108.

The piezo ultrasonic transducer system 115 according to an exemplary embodiment of the present invention may receive and analyze data from the ultrasound transponder 108 regarding the fullness of an individual's stomach. Data collected may be the ultrasonic signal received by ultrasound transponder 108 after emitting 1D, 2D or 3D ultrasound waves. The ultrasound transponder 108 may be active continuously, at pre-defined intervals or triggered by the user activating it or through a user interface on a smartphone or the like. The ultrasound transponder 108 may also be triggered to take measurements by software such as a mobile app (e.g. when there are indicators that a person is overeating), which may be stored in the remote device 113.

The ultrasonic signal may be analyzed to infer the degree of gastric filling from the resonant frequency as the stomach fills. The resonant frequency may change in terms of both amplitude and center frequency shift. This is readily detectable and measureable using the ultrasound transponder 108. Over several filling and emptying cycles a baseline may be established for a given individual and subsequently used to estimate the degree of filling. Analysis may include comparison to previous readings at different time points in the past. That is, baseline resonant frequencies may be dynamically recorded for an individual to determine baseline emptiness and fullness of the stomach, as well as partial fullness (e.g., 50% full). The baseline resonant frequencies may be stored by the system according to exemplary embodiments of the present invention, and newly detected resonant frequencies may be compared to the baseline resonant frequencies to increase accuracy of stomach fullness detection for an individual.

According to an exemplary embodiment of the present invention, the system can be calibrated using measurements taken when the user is fasting and then following a standard liquid or solid meal. Alternatively, user input (e.g., degree of satiety or perceived fullness) can be used for calibration. The system can further be calibrated by comparing readings to those obtained using other imaging modalities such as a medical ultrasound device, contrast material swallowing X-ray studies, computed tomography, MRI, or scintigraphy. Input from other sensors such as an accelerometer may be used to infer the user's position (e.g. sitting/standing, supine/prone) and calibrate readings accordingly.

According to an exemplary embodiment of the present invention ultrasound data analysis may be done using the microprocessor 104 and/or on the remote device 113 (e.g., by the remote device microprocessor 111). Thus, the system may be embodied in a standalone device or the system may be partially embodied in the ultrasound transponder 108 and partially embodied in the remote device 113.

The ultrasound transponder 108 may be constructed in a relatively simple form as a disc of piezoelectric material such as Kynar® encapsulated in a polymer and acoustically coupled to the body using gel. The ultrasound transponder 108 may be driven by the frequency generator 103 and the first amplifier 102. The reflected signal may be received by the second amplifier 107 and the analog to digital converter 106. The above elements can be packaged in a foul' that interfaces to a smartphone using a USB or wireless connection for both signal and device power. A processing device including an embedded stored program (e.g., an App) can be executed to cause a pulse of a desired frequency to be emitted by the ultrasound transponder 108 and then listen for the reflected signal. This signal can then be analyzed by methods familiar to those skilled in the art including but not limited to fourier analysis to determine the resonant frequency of the stomach and its magnitude. From this data an estimate can be created from the baseline information to determine the state of gastric fullness. This information can then be relayed from the smartphone or to a remote server via WiFi or GPRS, for example. At substantially the same time the user can be informed via auditory alarm, text message or visual display on the smartphone of their stomach fullness status. The remote server may also be used to store the data history, inform physicians, and utilize alternate methods to alert the patient of their status.

According to an exemplary embodiment of the present invention transmission of data from the system to an external computer can be continuous, programmed to occur at pre-defined times or intervals, or be triggered by user request (e.g. through a smartphone application). Changes in a particular magnitude of recorded data or arrival at a threshold level of fullness or emptiness of the stomach can trigger data to be transmitted from the system or a visual/tactile or sound alert to be fired by the device.

The system according to an exemplary embodiment of the present invention may be connected with a continuous glucose monitor, an insulin pump or a bionic pancreas to validate glucose readings, to indicate when a person is eating prior to glucose level rise. Sensing of gastric filling may indicate that glucose levels are about to rise, and be used to administer insulin early, thus preventing steep glucose rise and enabling the use of lower insulin doses. For instance, the system can inform an insulin pump system that a person has ingested food, triggering an alert to the user to add an insulin dose if they have not done it. Or, the degree of filling may be used in automated predictions of near future glucose levels by an insulin pump system to adjust automatic insulin dosing. The system according to an exemplary embodiment of the present invention may be used to cross-validate glucose readings by a glucose sensor. For instance, if a glucose sensor reports a rise in glucose levels at a time when it is not expected according to estimated insulin level, a preceding signal of gastric filling may be used to validate the glucose sensor.

According to an exemplary embodiment of the present invention, the user of the system may receive notifications or information by sound, light or vibration, or through a miniature screen display. For example, interaction with a user may occur through a user interface that may be used for user education, coaching on healthier eating habits, management of chronic diseases such as diabetes, or increasing awareness to fullness level after a bariatric or other abdominal surgery. The kinetics of gastric emptying may be inferred from the sensor and used in the diagnosis of gut motility disorders, or to infer the composition of the gastric content (as gastric emptying is related to its osmotic pressure, fat content and particle size). According to an exemplary embodiment of the present invention signals may be received by smartphone or other device with computational power and compared with annotated signals of the user and with signal patterns from other users. This may be used to derive the estimated degree of fullness, estimated ingested volume and rate (e.g., taking into account fluids secreted by the stomach mucosa), estimated outflow volume and rate, estimated time to stomach emptying. If these estimates fall out of the normal range, a diagnosis may be suggested.

The system according to an exemplary embodiment of the present invention may provide user coaching feedback such as an advice to refrain from eating at the time being or for some time until stomach is filled, to reduce speed of eating, to stop eating at a certain fullness threshold. Interaction with user may be by text, graphs, plots, or animation, for example, and may use visual, audio or vocal communication. The system may interact with a smart watch, headphones or other devices.

According to an exemplary embodiment of the present invention the stored program may be embedded in the smartphone. The smartphone may execute the stored program to output the alert data audibly or visually. The smartphone may execute the stored program to activate the ultrasound transponder at a preset interval including continuously or upon user activation.

According to an exemplary embodiment of the present invention at least one of the memory 116 or the stored program may be cloud-based and may be accessible via wireless communication.

According to an exemplary embodiment of the present invention, a wifi signal may be configured to establish communication with a portable processing device.

According to an exemplary embodiment of the present invention the remote device 113 (e.g., the portable processing device) may be at least one of a smartphone, a smart wearable device, a smart tablet, or a laptop computer.

According to an exemplary embodiment of the present invention the portable processing device may execute the stored program to output the alert data audibly or visually.

According to an exemplary embodiment of the present invention the portable processing device may execute the stored program to activate the ultrasound transponder at a preset interval including continuously or upon user activation.

According to an exemplary embodiment of the present invention the processor (e.g., the microprocessor 104 or the remote device microprocessor 111) may execute the stored program to perform analysis of the fullness data in connection with glucose data received from an external device.

According to an exemplary embodiment of the present invention the ultrasound transponder may be adhered or strapped to a portion of a user's skin proximal to the user's stomach.

According to an exemplary embodiment of the present invention an accelerometer may determine the position of the user.

Figure 2:
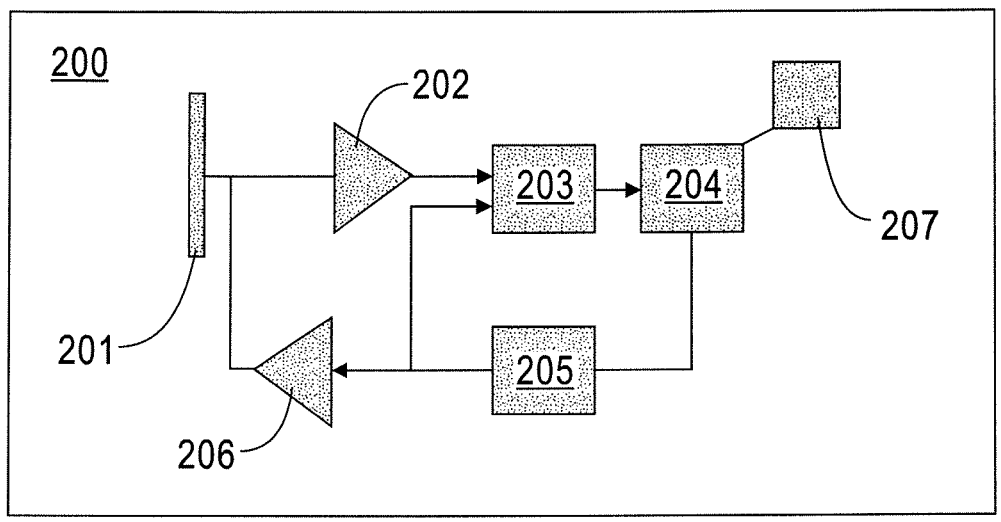
FIG. 2 illustrates an ultrasonic transducer system according to an exemplary embodiment of the present invention.

FIG. 2 illustrates an ultrasonic transducer system according to an exemplary embodiment of the present invention.

Referring to FIG. 2, an ultrasonic transducer system 200 may include an ultrasound transponder 201 (e.g., a piezo ultrasonic transducer), a processor and transmitter 204, a memory 207, an analog to digital converter 203, a second amplifier 202, a first amplifier 206 and a digital to analog converter 205. According to an exemplary embodiment of the present invention the ultrasonic transducer system 200 may be a standalone device.

According to an exemplary embodiment of the present invention an input frequency may be applied to the first amplifier 206 that applies an impedance matched input signal to the ultrasound transponder 201. The ultrasound transponder 108 may vibrate in response to the voltage input from the first amplifier 206, thus producing an ultrasonic acoustic signal. By varying the input frequency, it is possible to examine the acoustic transmission spectrum of the stomach compartment. This may be performed over a range of frequencies, for example, from 25 kHz to 1.5 MHz. The reflected acoustic signal may be captured by the ultrasound transponder 201 and may cause a voltage to be produced in the ultrasound transponder 201 that is compared to the voltage input. The reflected acoustic signal may be transmitted from the ultrasound transponder 201 to the second amplifier 202. The signal may pass through the analog to digital converter 203. The signal may be analyzed by the processor and transmitter 204 to determine a degree of stomach fullness. An analysis may be output (e.g., wirelessly transmitted) to an external device (e.g., a smartphone, a laptop or a cloud service) using ultrasound waves, IR, Bluetooth, or RFID.

According to an exemplary embodiment of the present invention the ultrasonic signal may be analyzed to infer the degree of gastric filling from the resonant frequency as the stomach fills. The resonant frequency may change in terms of both amplitude and center frequency shift. This is readily detectable and measureable using the ultrasound transponder 201. Over several filling and emptying cycles a baseline may be established for a given individual and subsequently used to estimate the degree of filling. Analysis may include comparison to previous readings at different time points in the past. That is, baseline resonant frequencies may be dynamically recorded for an individual to determine baseline emptiness and fullness of the stomach, as well as partial fullness (e.g., 50% full). The baseline resonant frequencies may be stored by the system according to exemplary embodiments of the present invention, and newly detected resonant frequencies may be compared to the baseline resonant frequencies to increase accuracy of stomach fullness detection for an individual.

According to an exemplary embodiment of the present invention, the system can be calibrated using measurements taken when the user is fasting and then following a standard liquid or solid meal. Alternatively, user input (e.g., degree of satiety or perceived fullness) can be used for calibration. The system can further be calibrated by comparing readings to those obtained using other imaging modalities such as a medical ultrasound device, contrast material swallowing X-ray studies, computed tomography, MRI, or scintigraphy. Input from other sensors such as an accelerometer may be used to infer the user's position (e.g. sitting/standing, supine/prone) and calibrate readings accordingly.

Figure 3:
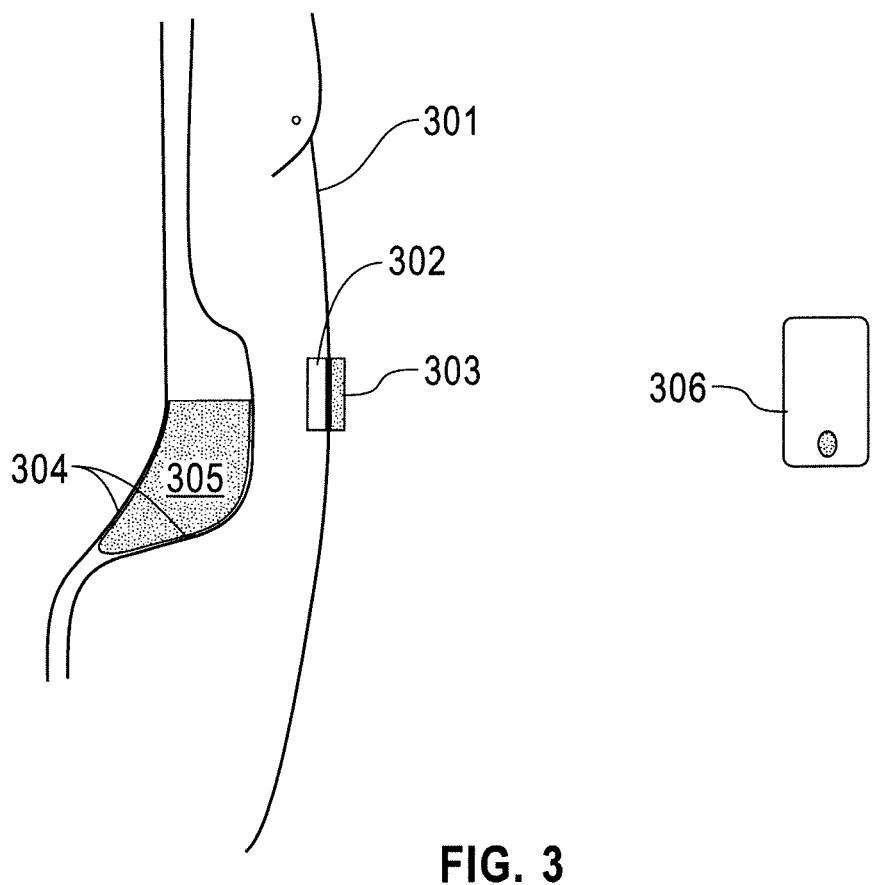
FIG. 3 illustrates a gastric fullness sensor measuring stomach fullness according to an exemplary embodiment of the present invention.

FIG. 3 illustrates a gastric fullness sensor measuring stomach fullness according to an exemplary embodiment of the present invention.

Referring to FIG. 3, a gastric fullness sensor 303 may be secured to an abdomen 301 of an individual by a securing part 302. The gastric fullness sensor 303 may measure stomach contents 305 of the individual by detecting the stomach walls 304 (e.g., front and back stomach walls) of the individual. The gastric fullness sensor 303 may communicate with an external device 306. The securing part 302 may be substantially the same as the securing part described above, and duplicative descriptions may be omitted. The external device 306 may be substantially the same as the remote device described above, and duplicative descriptions may be omitted. The terms "remote device" and "external device" may be used interchangeably herein.

The gastric fullness sensor 303 may include the system for monitoring stomach fullness or the ultrasonic transducer system described above with reference to FIGS. 1 and 2.

According to an exemplary embodiment of the present invention the gastric fullness sensor 303 may be secured to the abdominal, thoracic or flank regions of the individual using an adhesive patch. The sensor may use ultrasound to measure the distance between stomach walls 304 and based on this information may provide an estimation for the volume of stomach content. Data captured can be analyzed and stored within the gastric fullness sensor 303 or may be wirelessly transmitted to the external device 306. The gastric fullness sensor 303 and/or the external device 306 may include a memory and a processor according to exemplary embodiments of the present invention. According to an exemplary embodiment of the present invention the distance between the front and rear walls of the stomach may be measured by the ultrasound signal and used with other data including but not limited to the patients weight, height, age and sex to estimate the degree of fullness of the stomach.

According to an exemplary embodiment of the present invention variations in stomach fullness over time may be measured by taking multiple measurements over a period of time to estimate stomach activity (e.g., stomach contractions) that are further indicators of fullness.

According to an exemplary embodiment of the present invention the gastric fullness sensor 303 may be used as an audio microphone to detect and localize sounds originating in the stomach. This may be done by detecting sound intensity to infer proximity or by using a plurality of gastric fullness sensors 303 to determine the origin position of the detected sound.

According to an exemplary embodiment of the present invention the combination of ultrasonic dimensional measurement, physical motion measurement and acoustic signal detection and position estimation may be used to estimate the level of stomach activity and fullness.

According to an exemplary embodiment of the present invention the gastric fullness sensor (e.g., the gastric fullness sensor 303) may be a miniature device attached to the person's skin overlying the stomach (e.g., on the upper left abdominal quadrant). According to an exemplary embodiment of the present invention the gastric fullness sensor (e.g., the gastric fullness sensor 303) may be positioned on the skin of any part of the abdomen, chest or flank. According to an exemplary embodiment of the present invention the gastric fullness sensor (e.g., the gastric fullness sensor 303) may be handheld and placed in contact with the skin overlying the stomach when a user would like to get a measurement of the gastric filling level. The device may be stand-alone or integrated with another device such as a smartphone, a smart watch, or a digital pen, for example. However, exemplary embodiments of the present invention are not limited to integration with a particular external device, and any desired external device may be used.

Figure 4:
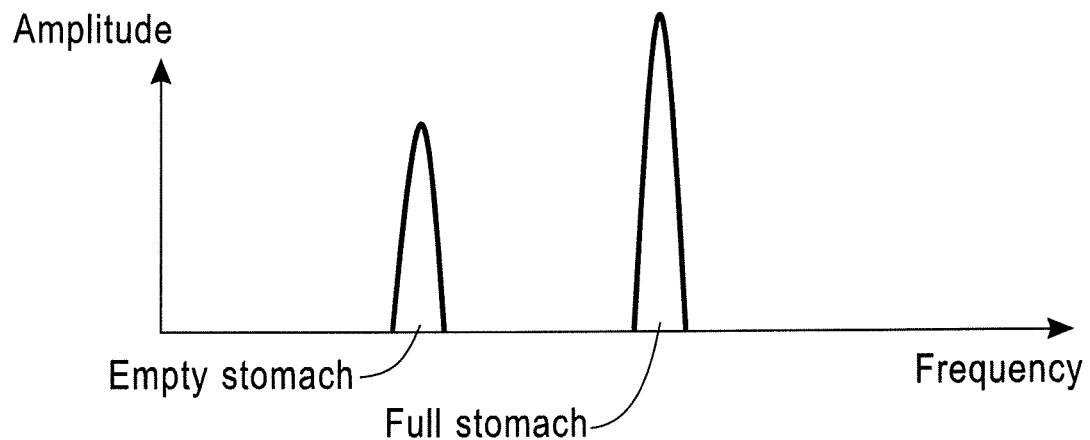
FIG. 4 illustrates a graph showing exemplary gastric fullness signal amplitudes according to an exemplary embodiment of the present invention.

FIG. 4 illustrates a chart showing exemplary gastric fullness signal amplitudes according to an exemplary embodiment of the present invention.

Referring to FIG. 4, according to an exemplary embodiment of the present invention an input frequency may be applied to the first amplifier that applies an impedance matched input signal to the ultrasound transponder. The ultrasound transponder may vibrate in response to the voltage input from the first amplifier, thus producing an ultrasonic acoustic signal. By varying the input frequency, it is possible to examine the acoustic transmission spectrum of the stomach compartment. This may be performed over a range of frequencies, for example, from 25 kHz to 1.5 MHz. The reflected acoustic signal may be captured by the ultrasound transponder and may cause a voltage to be produced in the ultrasound transponder that is compared to the voltage input. The reflected acoustic signal may be transmitted from the ultrasound transponder to the second amplifier. The signal may pass through the analog to digital converter. The signal may be analyzed by the processor and transmitter to determine a degree of stomach fullness. An analysis may be output (e.g., wirelessly transmitted) to an external device (e.g., a smartphone, a laptop or a cloud service) using ultrasound waves, IR, Bluetooth, or RFID.

According to an exemplary embodiment of the present invention the ultrasonic signal may be analyzed to infer the degree of gastric filling from the resonant frequency as the stomach fills. The resonant frequency may change in terms of both amplitude and center frequency shift. This is readily detectable and measureable using the ultrasound transponder. Over several filling and emptying cycles a baseline may be established for a given individual and subsequently used to estimate the degree of filling. Analysis may include comparison to previous readings at different time points in the past. That is, baseline resonant frequencies may be dynamically recorded for an individual to determine baseline emptiness and fullness of the stomach, as well as partial fullness (e.g., 50% full). The baseline resonant frequencies may be stored by the system according to exemplary embodiments of the present invention, and newly detected resonant frequencies may be compared to the baseline resonant frequencies to increase accuracy of stomach fullness detection for an individual.

According to an exemplary embodiment of the present invention, the system can be calibrated using measurements taken when the user is fasting and then following a standard liquid or solid meal. Alternatively, user input (e.g., degree of satiety or perceived fullness) can be used for calibration. The system can further be calibrated by comparing readings to those obtained using other imaging modalities such as a medical ultrasound device, contrast material swallowing X-ray studies, computed tomography, MRI, or scintigraphy. Input from other sensors such as an accelerometer may be used to infer the user's position (e.g. sitting/standing, supine/prone) and calibrate readings accordingly.

According to an exemplary embodiment of the present invention, the reflected acoustic signal may be plotted onto a graph (e.g., the graph illustrated in FIG. 4). A reflected acoustic signal indicating an empty stomach may have a relatively smaller amplitude than a reflected acoustic signal indicating a full stomach measurement. The scale of the Y axis (e.g., amplitude) may be calibrated for each individual according to each individual's baseline measurements for a full or empty stomach. For example, some individuals may have a relatively large stomach (e.g., greater distance between the front and rear walls of the stomach) while some individuals may have a relatively small stomach (e.g., smaller distance between the front and rear walls of the stomach). Thus, the amplitudes of the reflected acoustic signals observed between individuals may vary, and the system according to exemplary embodiments of the present invention may dynamically adjust to account for individual differences (e.g., by machine learning).

Figure 5:
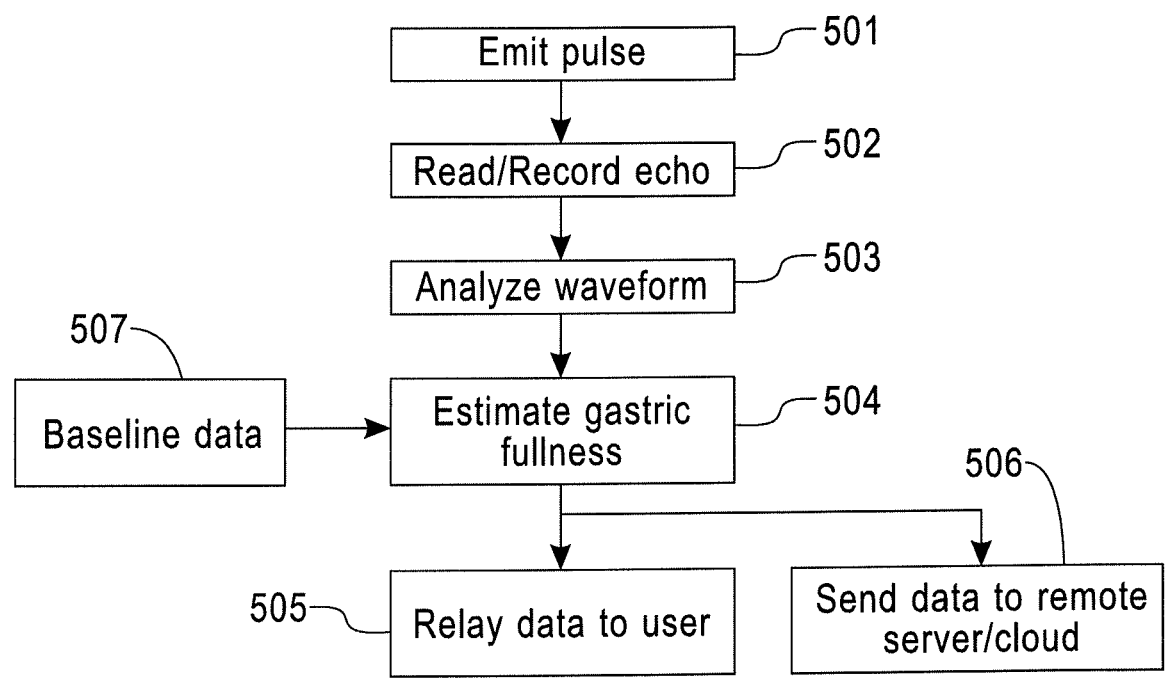
FIG. 5 illustrates a method of measuring stomach fullness according to an exemplary embodiment of the present invention.

FIG. 5 illustrates a method of measuring stomach fullness according to an exemplary embodiment of the present invention.

Referring to FIG. 5, a method of measuring stomach fullness may include emitting a pulse 501 (e.g., an acoustic signal according to exemplary embodiments of the present invention), reading/recording an echo 502, analyzing a waveform of the echo 503 and estimating gastric fullness 504. An initial estimate of gastric fullness may be made using baseline data 507. Data regarding gastric fullness may be relayed to a user 505. Gastric fullness data may be sent to a remote server/cloud 506.

According to an exemplary embodiment of the present invention the baseline data 507 may include height, weight and/or age data for an individual and may be used to initially estimate gastric fullness as a baseline. Baseline estimates of gastric fullness may be improved over time by dynamically learning the characteristics of an individual's stomach (e.g., maximum and minimum stomach volumes, rate of filling, contraction rate, stomach emptying rate). Baseline data 507 may be improved over time by the system according to exemplary embodiments of the present invention, such as through machine learning.

According to exemplary embodiments of the present invention, the method of measuring gastric fullness may be performed intermittently, continuously or on demand by the user. The user may be informed on the actual stomach volume, degree of fullness and/or predicted degree of fullness at a point of time in the future. The user may be notified when the stomach reaches a predetermined fullness threshold or is expected to reach such threshold in the near future. The user may be informed of stomach fullness by sound, light, and/or vibration emitted by the device. The user may be informed of stomach fullness by visual, tactile or sound notification from an external device such as a computer, a smartphone or smart watch.

The system and method according to exemplary embodiments of the present invention may be used or performed by a medical caregiver to determine the contents within the stomach of a patient. For example, the system and method according to exemplary embodiments of the present invention may be used to determine if a patient's stomach is sufficiently empty for surgery and/or to anesthetize the patient for surgery.

Figure 6:
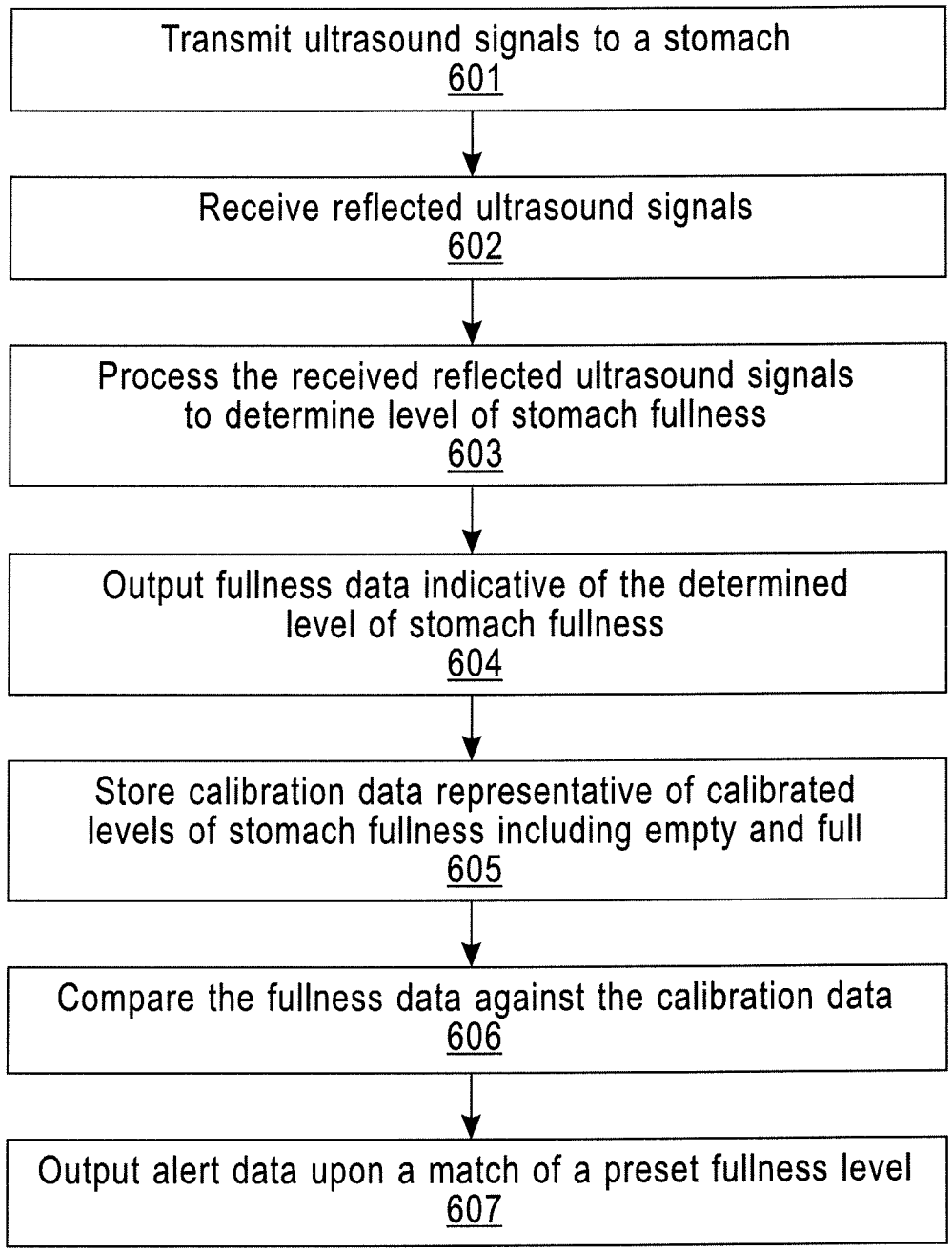
FIG. 6 illustrates a method of measuring stomach fullness according to an exemplary embodiment of the present invention.

FIG. 6 illustrates a method of measuring stomach fullness according to an exemplary embodiment of the present invention.

Referring to FIG. 6, an exemplary embodiment of the present invention provides a method of monitoring stomach fullness. The method includes transmitting ultrasound signals to a stomach 601. Reflected ultrasound signals may be received 602. The received reflected ultrasound signals may be processed to determine a level of stomach fullness 603. Fullness data indicative of the determined level of stomach fullness may be output 604. Calibration data representative of calibrated levels of stomach fullness including empty and full may be stored 605. The fullness data may be compared against the calibration data 606. Alert data may be output upon a match of a preset fullness level 607.

According to an exemplary embodiment of the present invention a method of monitoring stomach fullness may include wirelessly transmitting the fullness data to a processing device.

According to an exemplary embodiment of the present invention a method of monitoring stomach fullness may include wirelessly communicating from the processing device a control signal to control transmitting ultrasound signals at a preset interval including continuously or upon user activation.

According to an exemplary embodiment of the present invention alert data may be audibly or visibly presented at the processing device.

According to an exemplary embodiment of the present invention calibration data may be stored at a remote cloud-based storage device.

According to an exemplary embodiment of the present invention a method of monitoring stomach fullness may include comparing the fullness data against the calibration data at a remote cloud-based processing device.

According to an exemplary embodiment of the present invention fullness data may be analyzed in connection with glucose data received from an external device.

According to an exemplary embodiment of the present invention a method of monitoring stomach fullness may include determining a position of user by an accelerometer in connection with calibrating levels of stomach fullness.

Figure 7:
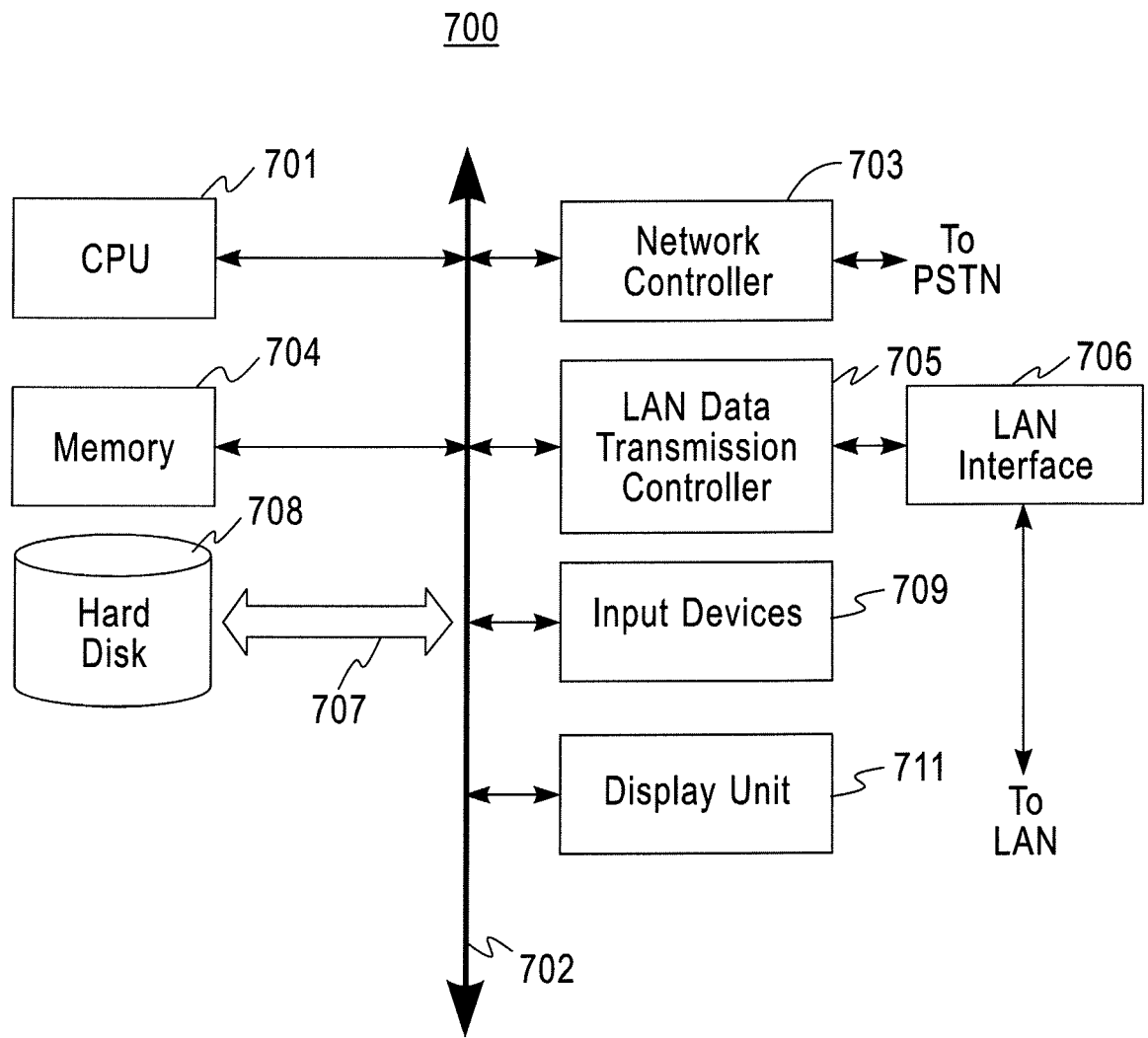
FIG. 7 illustrates a computer system usable to implement the methods according to exemplary embodiments of the present invention.

FIG. 7 illustrates a computer system usable to implement the methods according to exemplary embodiments of the present invention. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 700 may include, for example, a central processing unit (CPU) 701, random access memory (RAM) 704, a display unit 711, a local area network (LAN) data transmission controller 705, a LAN interface 706, a network controller 703, an internal bus 702, and one or more input devices 709, for example, a keyboard, mouse etc. As shown, the system 700 may be connected to a data storage device, for example, a hard disk, 708 via a link 707.

The descriptions of the various exemplary embodiments of the present invention have been presented for purposes of illustration, but are not intended to be exhaustive or limited to the exemplary embodiments disclosed. Many modifications and variations will be apparent to those of ordinary skill in the art without departing from the scope and spirit of the described exemplary embodiments. The terminology used herein was chosen to best explain the principles of the exemplary embodiments, or to enable others of ordinary skill in the art to understand exemplary embodiments described herein.

Figure 8:
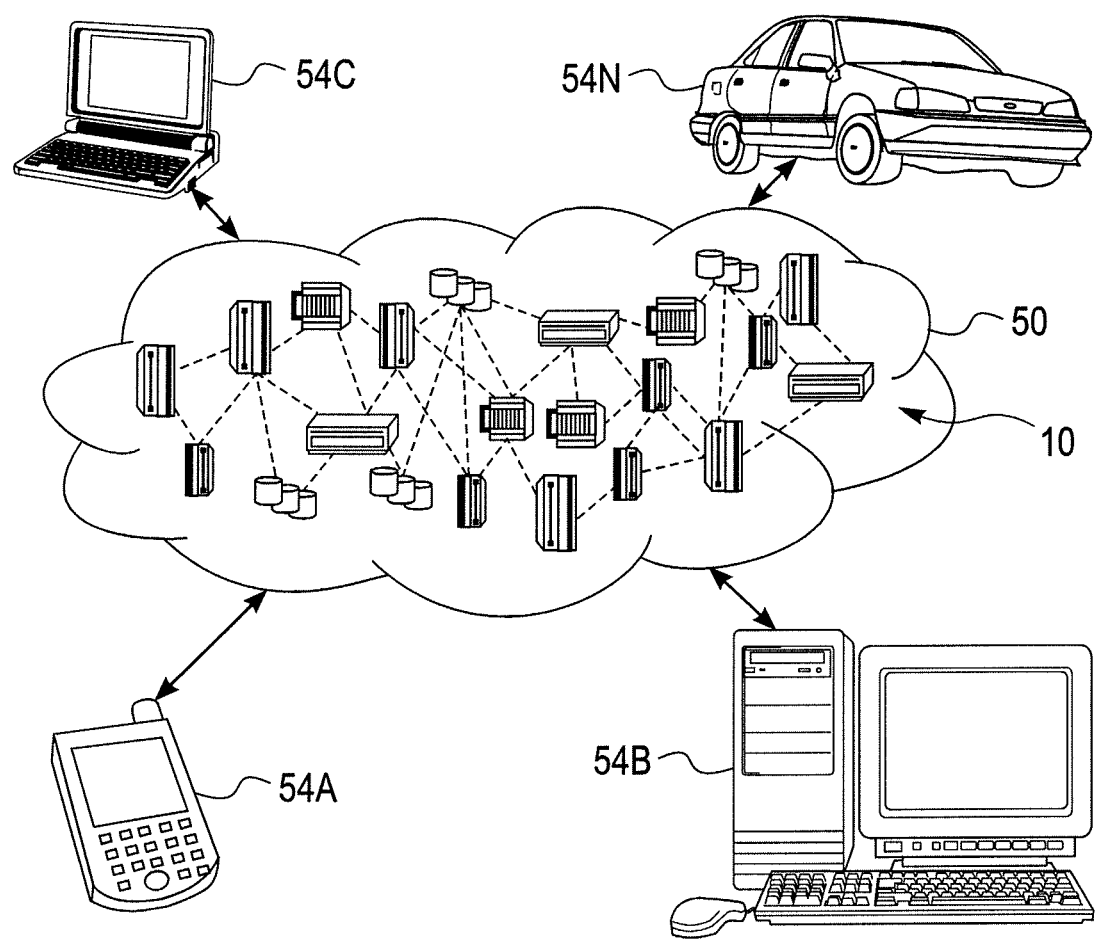
FIG. 8 depicts a cloud computing environment according to an embodiment of the present invention.
Figure 9:
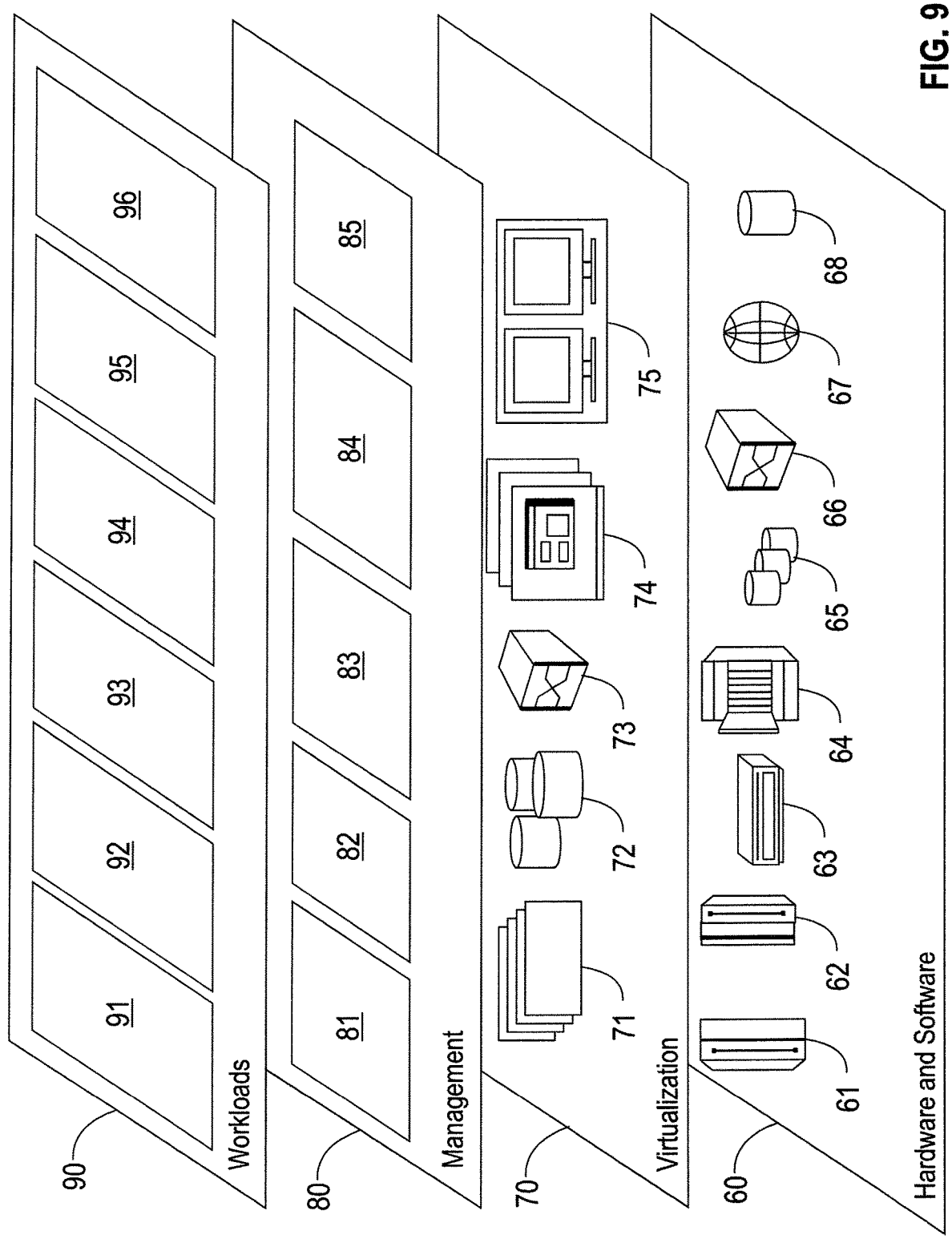
FIG. 9 depicts abstraction model layers according to an embodiment of the present invention.

FIG. 8 depicts a cloud computing environment according to an embodiment of the present invention. FIG. 9 depicts abstraction model layers according to an embodiment of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions (see, e.g., FIGS. 5 and 6).

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 8, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and message delivery determination 96. A system for measuring stomach fullness 96 may measure, analyze, record stomach fullness and transmit data regarding stomach fullness to one or more external devices exemplary embodiments of the present invention.

While the present invention has been particularly shown and described with reference to exemplary embodiments thereof, it will be understood by those of ordinary skill in the art that various changes in form and detail may be made therein without departing from the spirit and scope of the present invention as defined by the following claims.

The invention claimed is:

1. A system for monitoring stomach fullness, comprising:
   an ultrasound transponder configured to transmit ultrasound signals and receive reflected ultrasound signals;
   a processor configured to process the received reflected ultrasound signals to determine a level of stomach fullness and output fullness data indicative of the determined level of stomach fullness, wherein the determined level of stomach fullness is based on identified baseline information corresponding to measurements of a user;
   a memory configured to store calibration data representative of a plurality of calibrated levels of stomach fullness including empty and full; and
   a stored program having executable codes to, upon execution, control the ultrasound transponder, compare the fullness data against the calibration data, and output alert data upon a match of a preset fullness level.

2. The system of claim 1, wherein the stored program or the ultrasound transponder are embedded in a smartphone.

3. The system of claim 2, wherein the smartphone executes the stored program to output the alert data audibly or visually.

4. The system of claim 2, wherein the smartphone executes the stored program to activate the ultrasound transponder at a preset interval including continuously or upon user activation.

5. The system of claim 1, wherein at least one of the memory or the stored program is cloud-based and is accessible via wireless communication.

6. The system of claim 1, further including a wifi configured to establish communication with a portable processing device.

7. The system of claim 6, wherein the portable processing device is at least one of a smartphone, a smart wearable device, a smart tablet, or a laptop computer.

8. The system of claim 6, wherein the portable processing device executes the stored program to output the alert data audibly or visually.

9. The system of claim 6, wherein the portable processing device executes the stored program to activate the ultrasound transponder at a preset interval including continuously or upon user activation.

10. The system of claim 1, wherein the processor executes the stored program to perform analysis of the fullness data in connection with glucose data received from an external device, wherein a correctness of the glucose data is determined based on the fullness data.

11. The system of claim 1, wherein the ultrasound transponder is adhered or strapped to a portion of a user's skin proximal to the user's stomach.

12. The system of claim 1, further including an accelerometer to determine the position of the user and calibrate the determined level of stomach fullness based on the determined position of the user.

13. A method of monitoring stomach fullness, comprising:
   identifying baseline information corresponding to measurements of a user;
   transmitting ultrasound signals to a stomach of the user;
   receiving reflected ultrasound signals;
   processing the received reflected ultrasound signals and the baseline information to determine level of stomach fullness;

outputting fullness data indicative of the determined level of stomach fullness; storing calibration data representative of a plurality of calibrated levels of stomach fullness including empty and full;

comparing the fullness data against the calibration data; and outputting alert data upon a match of a preset fullness level.

14. The method of claim 13, further including wirelessly transmitting the fullness data to a processing device.

15. The method of claim 14, further including wirelessly communicating from the processing device a control signal to control transmitting ultrasound signals at a preset interval including continuously or upon user activation.

16. The method of claim 14, wherein the alert data is audibly or visibly presented at the processing device.

17. The method of claim 13, wherein the calibration data is stored at a remote cloud-based storage device.

18. The method of claim 13, wherein the comparing the fullness data against the calibration data is performed at a remote cloud-based processing device.

19. The method of claim 13, wherein the fullness data is analyzed in connection with glucose data received from an external device, wherein a correctness of the glucose data is determined based on the received reflected ultrasound signals.

20. The method of claim 13, further including determining position of the user by an accelerometer and calibrate the determined level of stomach fullness based on the determined position of the user.

* * * * *